US012669464B2

(12) United States Patent

Leon et al.

(10) Patent No.: US 12,669,464 B2

(45) Date of Patent: *Jun. 30, 2026

(54) MODULARIZED INEXPENSIVE DETECTION OF CEREBRAL SPINAL FLUID FOR MEDICAL APPLICATIONS

(71) Applicant: University of Florida Research Foundation, Inc., Gainesville, FL (US)

(72) Inventors: Marino Leon, Gainesville, FL (US); Brian C. Lobo, Gainesville, FL (US); Stephen J. Pearton, Gainesville, FL (US); Fan Ren, Gainesville, FL (US); Yu-Te Liao, Hsinchu City (TW)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 923 days.

This patent is subject to a terminal disclaimer.

(21) Appl. No.: 16/851,859

(22) Filed: Apr. 17, 2020

(65) Prior Publication Data

US 2020/0333286 A1 Oct. 22, 2020

Related U.S. Application Data

(60) Provisional application No. 62/835,962, filed on Apr. 18, 2019.

(51) Int. Cl.
*G01N 27/414* (2006.01)
*C07K 16/18* (2006.01)
(Continued)

(52) U.S. Cl.
CPC ......... *G01N 27/4145* (2013.01); *C07K 16/18* (2013.01); *G01N 27/227* (2013.01);
(Continued)

(58) Field of Classification Search
CPC ... G01N 27/327; G01N 27/4145; G01N 33/53
See application file for complete search history.

(56) References Cited

U.S. PATENT DOCUMENTS

| | | | |
|---|---|---|---|
| 4,464,581 | A | 8/1984 | Oritani |
| 9,316,637 | B2 | 4/2016 | Ren |
| | | (Continued) | |

FOREIGN PATENT DOCUMENTS

| | | | |
|---|---|---|---|
| CN | 104880557 | * | 2/2014 |
| CN | 104880557 A | * | 2/2014 |
| | | (Continued) | |

OTHER PUBLICATIONS

Syu et al. (Review—Field-Effect Transistor Biosensing: Devices and Clinical Applications, ECS Journal of Solid State Science and Technology, 7 (7) Q3196-Q3207 (2018)) (Year: 2018).*

(Continued)

*Primary Examiner* — Bao-Thuy L Nguyen
*Assistant Examiner* — Chau N.B. Tran
(74) *Attorney, Agent, or Firm* — Thomas | Horstemeyer, LLP

(57) ABSTRACT

Various examples are provided for disposable medical sensors that can be used for the detection of cerebral spinal fluid. In one example, a medical sensing system includes a disposable sensing unit comprising a functionalized sensing area disposed between electrodes; and a portable sensing unit analyzer including pulse generation circuitry that can generate synchronized gate and drain pulses and a transistor with a gate electrically coupled to one electrode. A gate pulse output of the pulse generation circuitry is electrically coupled to a second electrode and a drain pulse output is electrically coupled to a drain of the transistor. In another example, a method includes providing a sample to a functionalized sensing area, generating synchronized gate and (Continued)

drain pulses for a transistor, the gate pulse provided via the electrodes and functionalized sensing area, and sensing an output of the transistor that is a function of a target concentration of the sample.

15 Claims, 11 Drawing Sheets

(51) Int. Cl.

| | |
|---|---|
| *G01N 27/22* | (2006.01) |
| *G01N 33/487* | (2006.01) |
| *H10D 30/47* | (2025.01) |
| *H10D 62/10* | (2025.01) |
| *H10D 62/13* | (2025.01) |
| *H10D 64/60* | (2025.01) |

(52) U.S. Cl.
CPC ... *G01N 27/4148* (2013.01); *G01N 33/48707* (2013.01); *G01N 33/48785* (2013.01); *H10D 30/4732* (2025.01); *H10D 62/149* (2025.01); *H10D 64/605* (2025.01); *H10D 62/116* (2025.01)

(56) References Cited

U.S. PATENT DOCUMENTS

| | | | | |
|---|---|---|---|---|
| 2004/0002168 | A1* | 1/2004 | Remington | C07K 16/18 |
| | | | | 530/388.25 |
| 2005/0211559 | A1* | 9/2005 | Kayyem | G01N 27/3275 |
| | | | | 204/601 |
| 2009/0314644 | A1* | 12/2009 | Golan | C12M 47/04 |
| | | | | 204/600 |
| 2010/0188069 | A1 | 7/2010 | Ren | |
| 2010/0197524 | A1* | 8/2010 | Janata | G01N 33/5438 |
| | | | | 506/30 |
| 2011/0088456 | A1 | 4/2011 | Ren | |
| 2011/0159822 | A1* | 6/2011 | Kunishi | H03K 3/354 |
| | | | | 327/415 |
| 2014/0106338 | A1* | 4/2014 | Fischer | G01N 27/44791 |
| | | | | 435/7.1 |
| 2015/0160285 | A1 | 6/2015 | Joh | |
| 2015/0276667 | A1 | 10/2015 | Klootwijk | |
| 2015/0355129 | A1 | 12/2015 | Knopfmacher | |
| 2017/0350852 | A1 | 12/2017 | Lee | |
| 2018/0299403 | A1* | 10/2018 | Byrne | G01N 33/56911 |
| 2019/0170738 | A1 | 6/2019 | Ren | |

FOREIGN PATENT DOCUMENTS

| | | |
|---|---|---|
| KR | 20150111395 A | 10/2015 |
| WO | 2017153909 A1 | 9/2017 |

OTHER PUBLICATIONS

Teke and Morkoc (Group III Nitrides, Springer Handbook of Electronic and Photonic Materials, 2007) (Year: 2007).*

Molazemhosseini et al. (Single-Use Disposable Electrochemical Label-Free Immunosensor for Detection of Glycated Hemoglobin (HbA1c) Using Differential Pulse Voltammetry (DPV), Sensors 2016, 16(7), 1024). (Year: 2016).*

Yang ("Rapid detection of cardiac troponin I using antibody immobilized gate-pulsed AlGaN/GaN high electron mobility transistor structures", Appl. Phys. Letter., 2017 (Year: 2017).*

International search report for PCT/US20/55900 mailed Jan. 19, 2021.

Spiegel, et al., "The Extended Gate Chemically Sensitive Field Effect Transistor as Multi-Species Microprobe", Sensors and Actuators, 4 (1983).

Hsu, et al., "A package technology for miniaturized field effect transistor-based biosensors and the sensory array", ECS Journal of Solid State Science and Technology, 2017 6 Q63.

Shukla, et al., "Rapid detection strategies for the global threat of zika virus: current state, new hypotheses, and imitations", Frontiers in Microbiology, Published Oct. 24, 2016.

Sarangadharan, et al., "High sensitivity cardiac troponin I detection in physiological environment using ALGaN/GaN high electron mobility transistor (HEMT) biosensors", Elsevier, Biosensors and Bioelectronics, ScienceDirect (2018) 282-289.

Yang, et al., "Rapid detection of cardiac troponin I using antibody immobilized gate pulsued AlGaN/GaN high election mobility transistor structures", Appl. Phys. Lett. 111, Apr. 2021 (Nov. 2017).

Cary, et al., "Fast cerebrospinal fluid detection using inexpensive modular packaging with disposable testing strips", Journal of the The Electrochemical Society, Jan. 2019.

* cited by examiner

MODULARIZED INEXPENSIVE DETECTION OF CEREBRAL SPINAL FLUID FOR MEDICAL APPLICATIONS

CROSS REFERENCE TO RELATED APPLICATIONS

This application claims priority to, and the benefit of, U.S. provisional application entitled "Modularized Inexpensive Detection of Cerebral Spinal Fluid for Medical Applications" having Ser. No. 62/835,962, filed Apr. 18, 2019, which is hereby incorporated by reference in its entirety.

BACKGROUND

Cerebrospinal fluid (CSF) is a liquid found through the brain's ventricles and around the brain and spinal cord. CSF acts as a liquid transport for chemicals to and from the brain and maintains the cranial pressure, which acts as a cushion to the brain in case of sudden shocks. As CSF can act as a waste vehicle for neurons and other nervous system cells it must be replenished continuously. In a normal human adult there is 125 to 150 mL of CSF at one time, which is replenished every 6 hours, so approximately 600-700 mL of CSF is produced daily and thus leaks can be of significant quantity.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1:
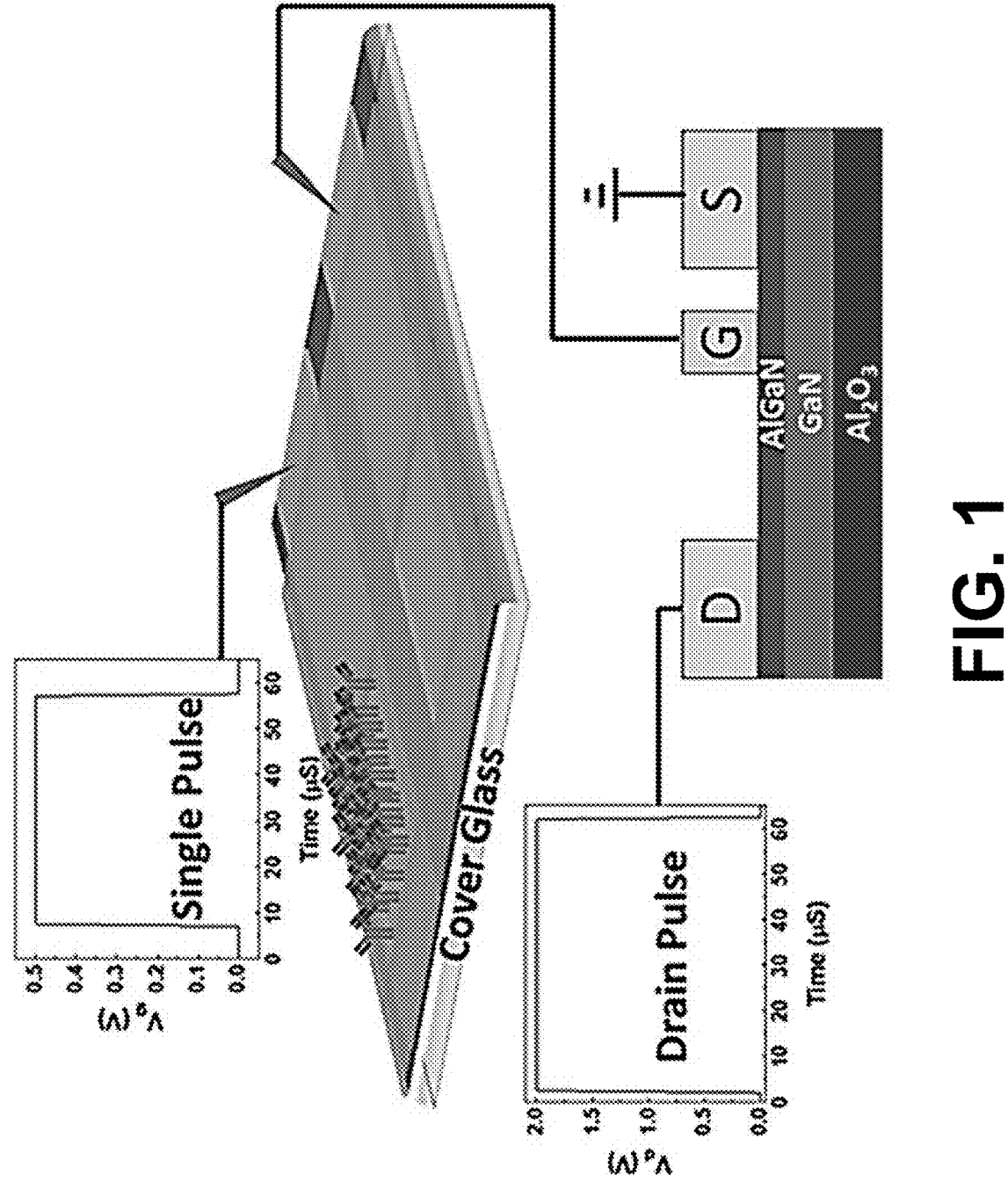
FIG. 1 is a schematic illustrating an example of a cover glass sensor, in accordance with various embodiments of the present disclosure.

Disclosed herein are various embodiments related to detection of cerebral spinal fluid using modularized, low cost, disposable medical sensors which can be fabricated on glass, paper or plastics, and applications thereof. Reference will now be made in detail to the description of the embodiments as illustrated in the drawings, wherein like reference numbers indicate like parts throughout the several views.

A cerebrospinal fluid (CSF) leak is a serious complication that can result from trauma to the skull base, otolaryngology (ENT) surgery, lumbar puncture, and on rare occasion purely spontaneously. The primary concern as a result of a leak is that bacteria can access the brain resulting in intracranial infection which left untreated can be deadly. Common symptoms include headache, nasal drainage, ear drainage, fever, and tinnitus. CSF leaks are traditionally detected through collection of the nasal/ear fluid, which undergoes analysis for the protein $\beta$-2-transferrin ($\beta$2T).

The $\beta$-2 conformation of transferrin is carbohydrate-free and exclusively found in CSF, not in blood, mucus or tears. It can also be found in patients with perilymph fluid leaks. Once a CSF leak has been detected establishing the location of the leak is the next step to determine whether endonasal endoscopic surgery is needed. High-Resolution Computed Tomographic (HRCT) scans are most commonly used for identification of the leak location as it provides 1 to 2 mm sections in the coronal and axial planes with algorithms for identification of bone to best identify the skull base defects which are causing the leaks. Surgery can be used to temporarily seal the leak so that the bone can repair itself and prevent infection until full recovery has occurred.

There are two primary methods of detection for a CSF leak: immunofixation electrophoresis (IFE) and enzyme-linked immunosorbent assay (ELISA); which are performed in a few reference laboratories and require multiple hour waiting periods, a trained technician to perform, and have poor lower limits of detection. IFE relies upon the separations of proteins by their molecular weight and as the $\beta$-2 conformation will traverse farther along an acidic gel than the $\beta$-1 due to being desialated. Consistent results have been demonstrated with IFE down to 2 $\mu$g/mL using samples from a patient, but this result required a 2.5 hour testing period not expedient enough for real time feedback during ENT surgeries. Additionally, to achieve good sensitivity and handle the inherently low concentration of $\beta$-2 transferrin in CSF, laboratory procedures have required samples to be concentrated by as much as 10-fold or the sample to be run in duplicate to ensure accurate detection.

In this context, the detection of $\beta$2T as a marker of CSF leakage through electrical sensing has been investigated. To alleviate the slow turn-around times of hospital laboratories and fairly limited lower limits of detection, electronic detection methods for proteins, viruses, or small molecules using biologically functionalized field effect transistors (FETs) have been considered. The exact method and biomarker vary, but the general backbone of the sensor is the FET. AlGaN/GaN high electron mobility transistors (HEMTs) can be utilized as the electron flow is generally within 50 nm of the surface and is easily modulated by changes in surface chemistry. By functionalizing the gate with an antibody, a change in drain current can be observed as a function of target concentration. Thus, bio-functionalized AlGaN/GaN HEMTs are considered due to their excellent sensing characteristics from the high-density electron channel located near-surface (about 25 nm).

Miniaturized portable electronic sensors that use an electrical signal to test for a biological marker offer a relatively straightforward method to address the need for accurate and near real time testing of CSF. However, the high cost of using GaN HEMT and the screening length of highly ionic solutions are concerns that should be addressed. For the sensing of proteins, the ability to function in highly ionic solutions such as whole blood, urine, saliva, etc. is important. The high ionicity can cause charge screening effects where the Debye screening length is shorter than that of the antibody/protein. To circumvent this issue, pulsing the sensor rather than applying a constant bias can provoke a spring-like response of the antibody-antigen complex which can be detected regardless of ionicity. A double pulse measurement can be utilized to produce the spring-like response of the antibody-protein complex.

The AlGaN/GaN HEMTs is also a limitation to modularization due to the high cost of the substrates which are prepared using low throughput methods, such as metal organic chemical vapor deposition, rather than through bulk growth methods like the Czochralski method for silicon. To allow for reuse of the sensing FET/HEMT and remove the need for specifically GaN HEMTs, the sensing portion of the device can be externalized through use of an electrode that feeds into the gate. By externalizing the sensing component from the HEMT, a testing strip can be replaced each time making the device reusable. With the sensing surface externalized, an inexpensive Si FET or other appropriate transistor technology (e.g., Si metal oxide semiconductor field effect transistor (MOSFETs), complementary MOSFETs (CMOSFETs), FinFETs, heterostructure high electron mobility transistors (HEMTs), bipolar transistors, or heterojunction bipolar transistors (HBTs)) can be used in place of the GaN HEMT. With these design considerations, the cost of modularizing such sensor platforms may be brought closer to the low cost of widely available glucose sensors.

In this disclosure, a disposable testing slide is externally integrated with a PCB board with a Si MOSFET to detect CSF from 0.1 ng/mL to 100 µg/mL. The designed platform externalized a Si metal-oxide-semiconductor FET (MOSFET) on a PCB with separate voltage controls for the drain and gate for customization for each individual biomarker, such that the same FET system can be used with only the antibody functionalized electrode being swapped. The PCB with circuitry for pulse generation, voltage adjustment and a Si MOSFET was designed to simplify the testing setup and drive the cost down by removing the need for expensive semiconductor parameter analyzers. Additionally, the disposable sensing electrode was manufactured on inexpensive microscope cover glass slides. The passivation used for the electrode was SU-8, as it is quite robust after curing and has extensive use for casting with PDMS, for the eventual goal of roll-to-roll manufacturing. The β2T sensor using the external PCB successfully detected from 0.1 ng/mL to 100 µg/mL of β2T in 1×PBS (1% BSA). A new sensing electrode was used for every test run and demonstrated strong uniformity between the fabricated sensing electrodes.

Referring to FIG. 1, shown is a schematic illustrating an example of a sensing unit with a cover glass functionalized with an antibody and separated from a bare electrode externally connected with an AlGaN/GaN HEMT. The AlGaN/GaN HEMT structure can be grown on a sapphire substrate with a low temperature AlN nucleation layer, 2.2 µm undoped GaN buffer layer, and 25 nm $Al_{0.25}Ga_{0.75}N$ barrier layer by metal organic chemical vapor deposition. Device isolation can be achieved with a $Cl_2$/Ar discharge in a Plasma Therm 790 inductively coupled plasma (ICP) system with 200 W ICP power and 50 W rf power at 2 and 13.56 MHz, respectively. The source and drain Ohmic contacts can be formed by e-beam evaporation with Ti/Al/Ni/Au (25/125/45/100 nm) with a standard lift-off process, and the contacts can be annealed at 850° C. for 45 s. Schottky gate contacts can be formed with e-beam deposition Ni/Au (20 nm/80 nm) and Ti/Au can be used as interconnection metals.

For the cover glass portion, two 100 µm wide metal lines of Ni/Au (20 nm/80 nm) separated by 20 µm can be fabricated using e-beam evaporation and standard lift-off. A 100 nm SiN, passivation layer can be deposited with a plasma enhanced chemical vapor deposition system to passivate the metal electrodes, and a 100 µm×100 µm contact window can be opened on both metal electrodes with buffered oxide etch (BOE). One of the contact windows can be treated by covering the other contact window with the photoresist, which can be subsequently stripped away. A pulsed gate voltage can be applied to the electrode fabricated on the cover glass and functionalized with the antibody, while a pulsed drain voltage is applied to the drain of HEMT.

A disposable sensing unit was fabricated on a disposable glass slide with the Ni/Au based (20 nm/80 nm) metal electrodes using e-beam evaporation and a standard lift-off process. The metal electrodes extend toward each other from opposite ends of the slide, and are separated by a defined distance. To passivate the electrodes, SU-8 photoresist was employed and opened on the sensing ends of the electrodes and on the contact windows. To immobilize anti β-2-transferrin antibody on the metal electrodes, the electrodes were treated with thioglycolic acid (TGA) for 12 hours at room temperature. Excess TGA was rinsed off using deionized (DI) water. The TGA thiol strongly binds to the Au surface and provides a carboxylic acid group to react with the amines of the antibody. The Au—S bond can form a strong bond with not additional reagents needed. The device was then incubated in a PBS solution of CSF monoclonal antibody. Anti β2T antibody was reacted at 4° C. for 4 hours only on the sensing ends of the electrodes. The sensing unit was then rinsed with DI water and phosphate buffer saline (PBS) to remove any excess unbound antibody. The sensor was stored at 4° C. in PBS when not in use.

The binding efficiency of the antibody to the gold surface is dependent on a case-by-case basis. If poor binding efficiency is noted (e.g., poor sensitivity to the target protein), a two-step chemical reaction can be used to improve and activate the surface carboxylic acids. This can be achieved by submerging the device first in a 0.1 mM solution of N,N'-dicyclohexylcarbodi-imide in acetonitrile for 30 minutes and then in a 0.1 mM solution of N-hydroxysuccinimide in dry acetonitrile for 1 hour. These functionalization steps result in the formation of succinimidyl ester groups on the gold of the sensing electrodes. Then incubating the device with the mAB of choice. For this study, these two steps were not needed as good sensitivity was noted. Previously, stability of the antibody on the sensor surface has been established for up to 9 months after initial fabrication without using these two steps To prevent non-specific surface binding interactions between unbound TGA and any competing off-target proteins, the TGA can be terminated by treatment with ethanolamine after incubation with the mAB.

Figure 2:
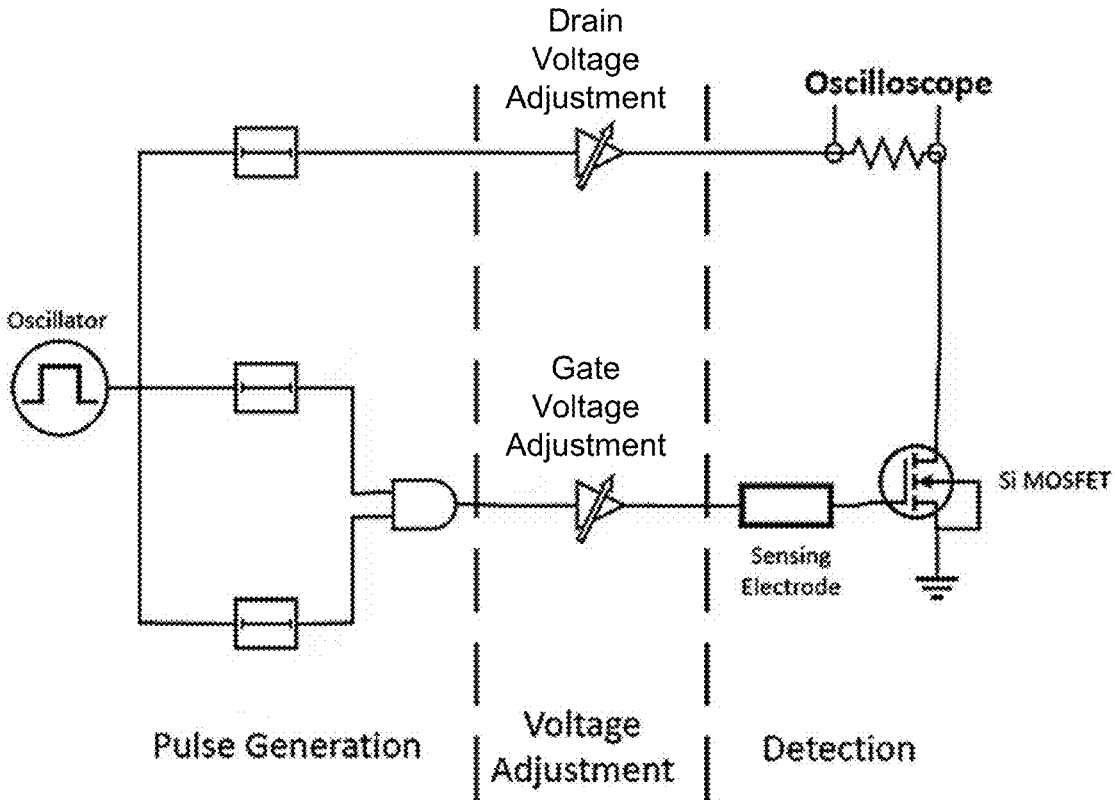
FIG. 2 is a schematic diagram illustrating an example of an electronic sensor including a disposable sensing unit, in accordance with various embodiments of the present disclosure.
Figure 3:
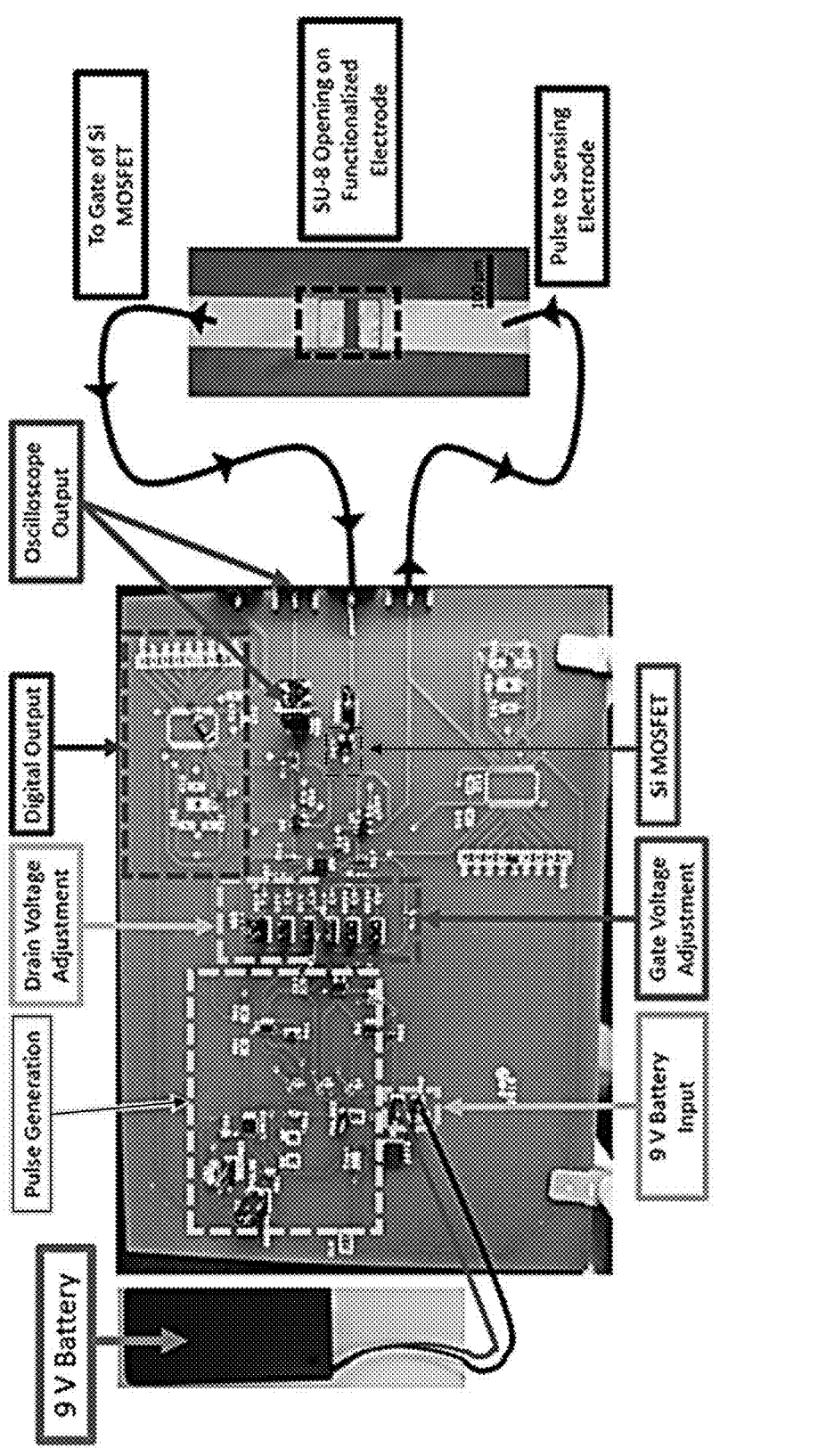
FIG. 3 is an image showing an implementation of the electronic sensor of FIG. 2 with the disposable sensing unit connected, in accordance with various embodiments of the present disclosure.

PCB Design and Setup. FIG. 2 is a schematic diagram illustrating the generalized PCB sensor design and FIG. 3 is an image of the implemented PCT circuitry connected to the electrodes of the disposable sensing unit. As illustrated in FIG. 2, the circuit includes three main functional blocks or sections: pulse generation, voltage level adjustment, and detection. As shown in FIG. 3, the pulse generation section is supplied by a 9 Volt battery through a battery input connection. The voltage adjustment section includes circuitry for both drain voltage adjustment and gate voltage adjustment shown in FIG. 3. The output of the gate voltage adjustment is supplied to a first electrode of the disposable sensing unit, and the second electrode is coupled to the gate of the transistor (e.g., Si MOSFET) as illustrated in FIG. 3. The output of the drain voltage adjustment is supplied to drain of the transistor via oscilloscope output connections as depicted in FIGS. 2 and 3. Digital output to an on-board display may also be implemented.

In the pulse generation section, a mono-stable oscillator followed by delay lines and gate generate pulses that are overlapping but with different widths. The gate voltage level adjustment allows for on PCB variation of the applied gate voltage supplied to the disposable sensing unit in order to optimize sensing on a protein-by-protein basis, rather than designing a new PCB for every sensing target. Furthermore, depending on a protein's length, net charge, and folding, the applied voltage needs to be roughly tuned such that the protein-antibody complex is perturbed and undergoes a spring-like relaxation. If insufficient voltage is supplied there will be no perturbation of the protein-antibody complex. If excessive voltage is applied there may be full elongation and dissociation of the protein-antibody complex. In either case sensing of the target protein will not occur repeatably. The drain current can also be adjusted by the drain voltage adjustment in order to tune the device for maximum transconductance. Detection of the target protein can be monitored via the drain current using an oscilloscope coupled across through a 50Ω resistor placed before the drain of the transistor.

Figure 4:
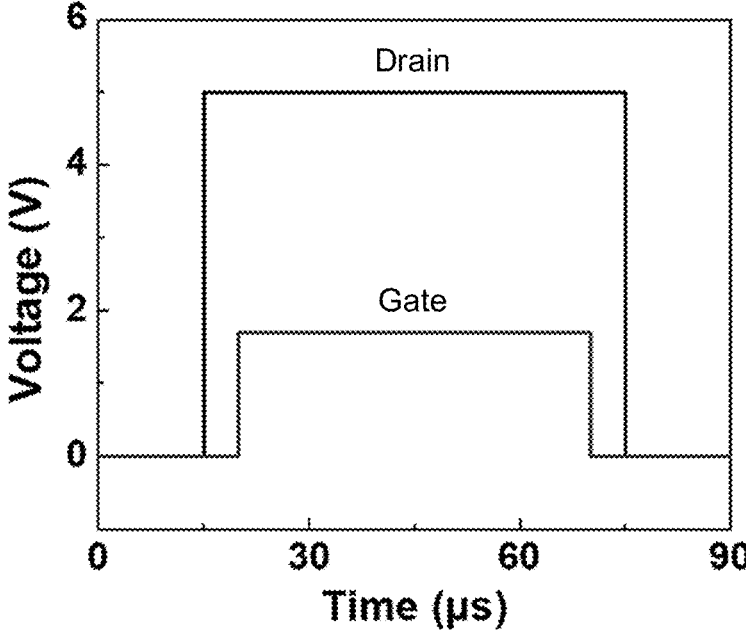
FIG. 4 illustrates examples of gate and drain pulses, in accordance with various embodiments of the present disclosure.

To test the fabricated PCT design and disposable sensing unit, human pooled CSF was serially diluted from 100 μg/mL to 0.1 ng/mL in pH 7.4 PBS and 1 wt % bovine serum albumin. Bovine serum albumin serves two purposes: to stabilize the proteins in solutions and to act as control for non-specific binding effects as the BSA is many orders of magnitude more concentrated than the target protein in solution. It is recognized that the concentration of CSF is not the concentration of β2T, but that it is actually much lower as it is only a minor constituent of CSF (<1 mg/L). Total protein content of CSF has been reported from 150 to 500 mg/L in healthy adults. To test the functionalized CSF sensor, the diluted CSF solution was applied to the sensing electrode and allowed to bind to the sensor surface for 5 minutes prior to measurement. Two synchronous pulses were applied to the D-mode Si MOSFET. The first was a 60 μs pulse to the drain, turning the device on, and 5 μs later a synchronous pulse was applied to the gate for 50 μs. For this study, the drain voltage was adjusted to $V_d$=5 V and the gate voltage was adjusted to $V_g$=1.7 V. FIG. 4 illustrates the relationship between the synchronous pulses. Additionally, in order to ensure detection at the lower limits of ng/mL, traces in the circuit were kept short in order to reduce noise from coupling.

Figure 5A:
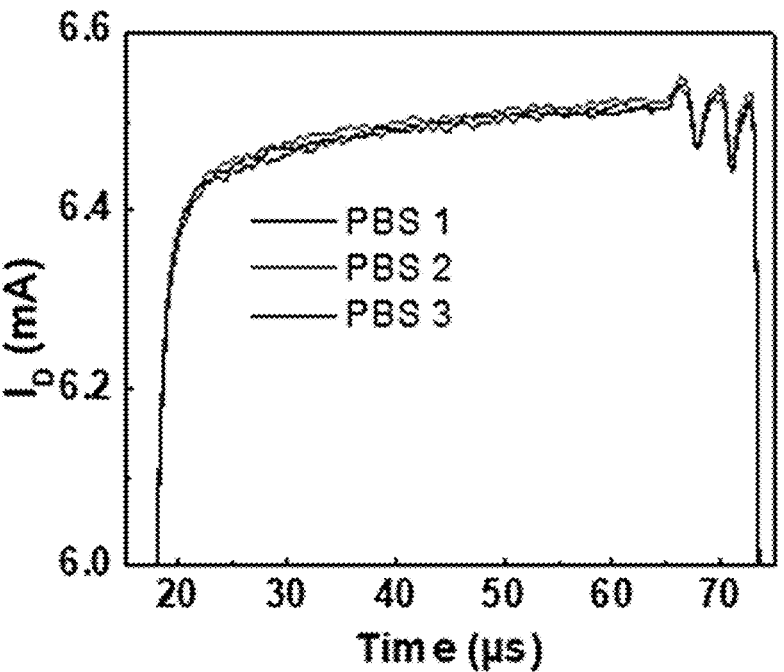
FIGS. 5A and 5B illustrate examples of drain current response using the electronic sensor of FIG. 2, in accordance with various embodiments of the present disclosure.
Figure 5B:
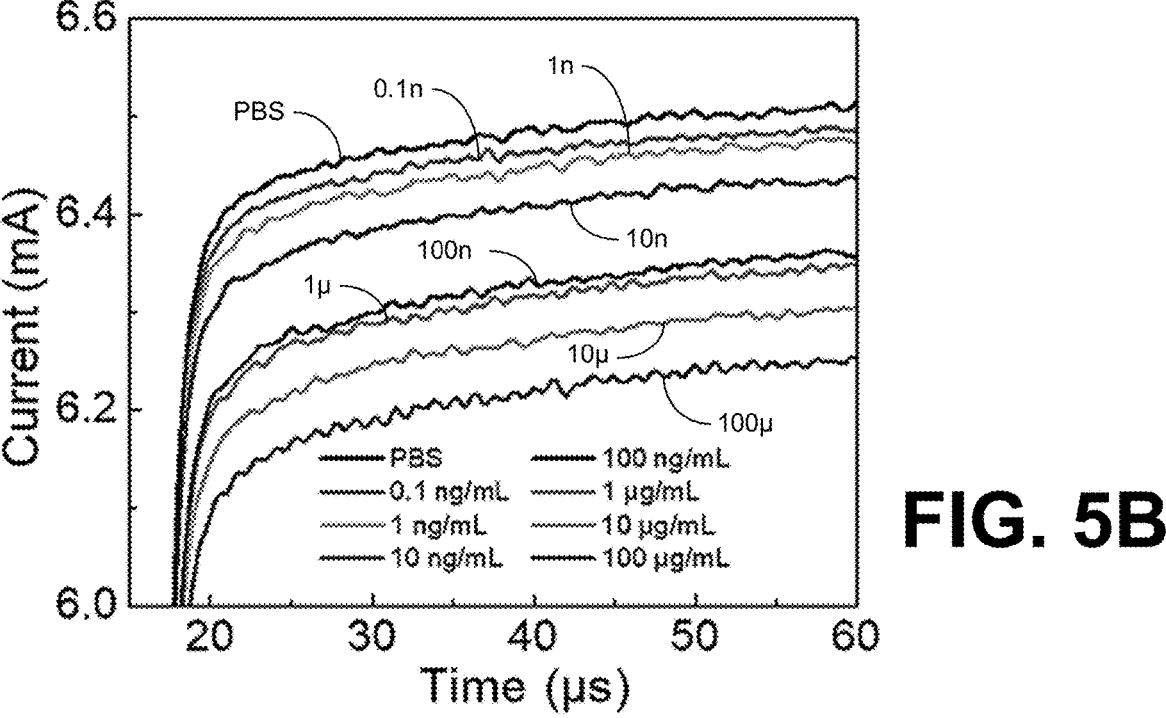

CSF Sensing. Referring to FIGS. 5A and 5B, shown are examples of time dependent detection of CSF dilutions using the implemented sensor design of FIGS. 2 and 3. To screen out defective sensors, PBS reference runs were performed three times subsequently. FIG. 5A contains an example of the output. The sensor was considered useful when all three measurements matched. FIG. 5B illustrates an example of time dependent detection of a range of CSF concentrations. The device currents for varying CSF concentrations from 0.1 ng/mL to 100 ng/mL are shown. The bend of the curves in FIG. 5B is the dynamic drain current response due to the double spring-like response of the perturbed antibody-protein complex. To achieve such low sensitivity (to the sub ng/mL range), noise of the designed PCB must be considered. From testing, it was found that use of a low noise DC power source, in our case a 9V battery, was needed rather than a DC power source which was plugged into a standard 60 Hz wall outlet. This issue may be mitigated by utilizing appropriate filters for an AC/DC power source. Additionally, the presented response is the average of 16 measurements, averaging of more measurements would lead to a smoother curve with less noise. A phosphate buffer saline (PBS) was tested to provide a baseline measurement.

Figure 6:
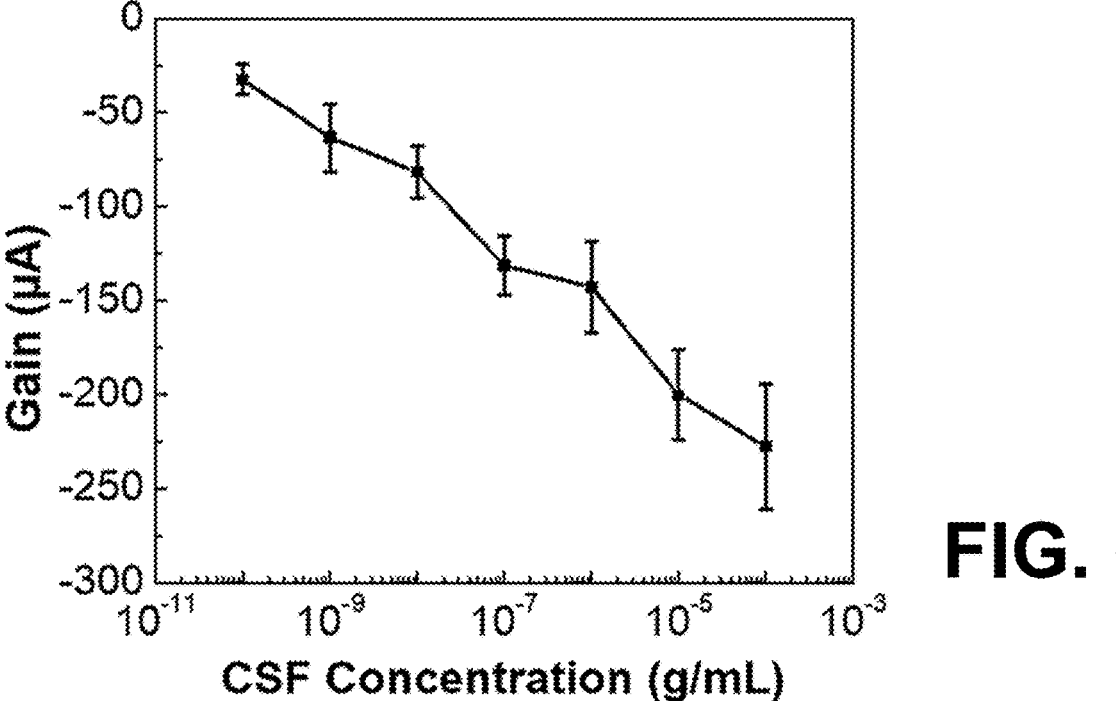
FIG. 6 illustrates an example of average sensor gains across different sensors, in accordance with various embodiments of the present disclosure.

Average gains across five separate sensors were also plotted in FIG. 6, to show the repeatability of such tests. While the sensing only targets the β2T (which is a very minor constituent of the CSF), the concentration of CSF as a whole is indicated. Normal CSF contains <1 g of all types of present proteins per 1 L of CSF; thus the actual tested concentration for β2T is at least 1000× fold more dilute than the stated CSF. The sensor has not reached saturation even at the very high concentration of 100 μg/mL of CSF. The antibody sensor coverage was calculated to be approximately $5×10^6$ antibody units on the sensing area.

Modelling of Sensor Gain. The antigen and antibody binding occurs through an active process which is reversible. Previous modelling attempts have used small molecule approximations, Langmuir Extended Isotherm, which provided good fits to relate the gain of the sensor to the target concentration. The Langmuir Extended Isotherm model for the change in drain current can be expressed as:

$$\Delta I = \frac{q_m b[C]^\eta}{1+b[C]^\eta}, \tag{1}$$

where $q_m$ and b are Langmuir constants, [C] is the concentration of the target in the test solution, and η is related to the spread of the energy distribution of the target. However, the small molecule approximation is not fully accurate when discussing antibodies and proteins as their sizes are in the 100's of kDa, thus steric hindrance is a serious consideration, especially when packed tightly on a surface. Additionally, with such large charged structures there will be electrostatic attraction and repulsion between neighboring ligands and between the functionalized surface of the sensing unit to the target protein in solution. For this purpose, a relation between solution concentration of the target protein and the fraction of the sensor surface which is bound was proposed by Stankowski et al as:

$$[C] = \frac{1}{K_0} \cdot \frac{\theta}{1-\theta} \cdot \exp\left(\frac{\theta}{1-\theta} + 2a\theta\right), \tag{2}$$

where $K_0$ is the effective initial rate constant of the antibody-protein binding, θ is the surface coverage, and a is a measure of the electrostatic repulsion of bound proteins on the sensor. The exponential term contains the two competing effects of steric hindrance and electrostatic repulsion. As coverage approaches saturation (0→1), the steric term $$\left(\frac{\theta}{1-\theta}\right)$$

will become dominant (asymptotically) as the protein covered surface is tightly packed and the likelihood of free proteins successfully entering and binding to free antibodies on the sensor is reduced.

Figure 7:
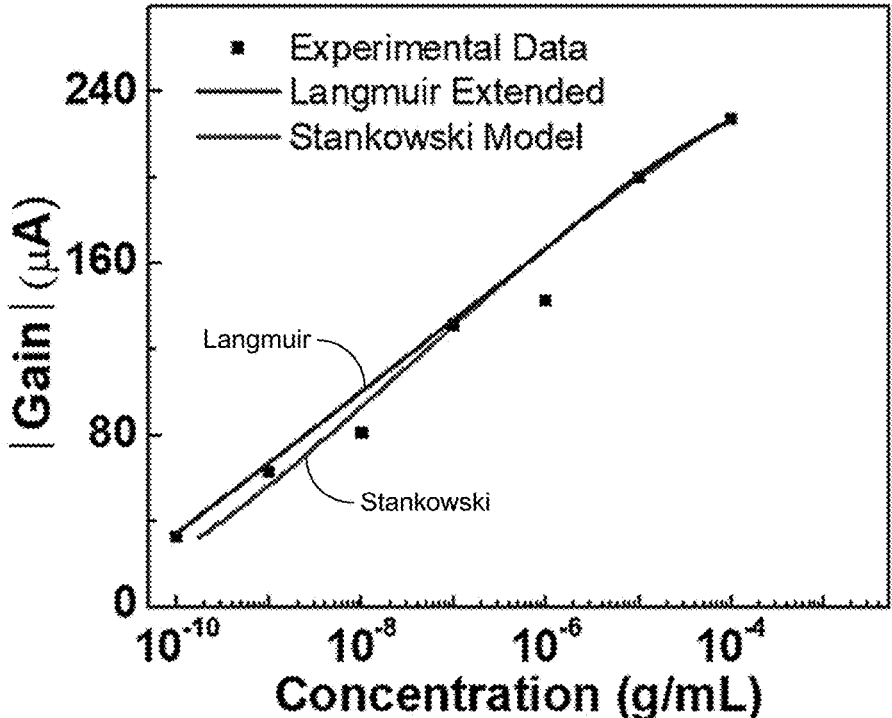
FIG. 7 illustrates a comparison of experimental data with the Langmuir Extended Isotherm and Stankowski models, in accordance with various embodiments of the present disclosure.

Referring next to FIG. 7, the experimental data was fit to both models and shown to have good agreement between the two. Agreement of the two models can be expected under low to medium coverage conditions. The Langmuir-Extended model can be expected to provide a good fit in regimes of low coverage of the sensor surface with the antibody where steric hindrance between neighboring proteins has not yet becoming a limiting factor. From the Langmuir model, the following constants were extracted $g_m$=311.8 μA, b=19.69 (L/g)$^{0.215}$, and η=0.215. It should be noted that $q_m$ is the maximum expected current change in the sensor at saturation. The Stankowski model provides some further elucidation on the sensor functionality and underlying mechanisms. The exact coverage of the sensor is not directly known but can be approximated by the change in sensor current with concentration such that:

$$\theta = \frac{n}{i} \sim \frac{\Delta I}{\Delta I_{max}}, \quad (3)$$

where n is the number of bound proteins to the sensor surface, and i is the total number of available antibodies on the sensor surface, $\Delta I$ is the experimental value of change in current, and $\Delta I_{max}$ is the change in current when the sensor surface has become saturated with the target protein. From the modeled fit $K_0$~2.57×10$^9$ mL/g, $\Delta I_{max}$=319 μA, and α=6.33. The positive value of a indicates a mild repulsion between antibody bound proteins. This repulsion is dominant at low to medium coverages of the sensor, but as the proteins begin to tightly pack on the surface steric hindrance will become dominant. Interestingly, the predicted maximum current change of $q_m$=311.8 μA and $\Delta I_{max}$=319 μA from the two models are similar and this provides some further confirmation of each result.

This disclosure has detailed the use of a Si MOSFET with the gate connected to a disposable antibody-functionalized electrode for the detection of cerebral spinal fluid (CSF). Through the design of the Si based PCB, the need for GaN HEMTs has been mitigated reducing the cost of production for commercial applications. Through the use of a double pulse method to the test electrode and the drain of the Si MOSFET, ionicity of the test solution is no longer a concern as a double layer is produced and perturbed on the test electrode giving rise to current changes related to the concentration of the biomarker. Additionally, the PCB provides connections for an oscilloscope readout or an onboard display entirely removing the need for any expensive semiconductor parameter analyzers. Clinically, the cutoff for a CSF leakage has traditionally been limited to about 2 μg/mL with the analysis taking several hours. With this newly designed electronic sensor, CSF can be detected at levels from 0.1 ng/mL to 100 μg/mL within 5 minutes, greatly improving the detection limits and feedback time for medical professionals.

In summary, cerebral spinal fluid (CSF) which is released when damages to the skull or spinal column have been incurred has been successfully detected from concentrations of 0.1 ng/mL to 100 μg/mL. This CSF testing method provides for selective sensing of β2T through use of traditional monoclonal antibodies. β-2-transferrin provides for selective sensing as it is only found in CSF. Both Langmuir Extended Isotherm and Stankowski models were employed to fit the experimental data. Design and implementation of an external PCB was successfully implemented with disposable testing strips in the process of bringing a true point of care detection platform to all hospital personnel.

The disclosed technology may be used to provide point of care testing in with a degree of precision that can avoid post-operative complications resulting from current tests being performed only at limited sites due to cost and expertise. The sensing electrode can be integrated on a disposable strip and can be utilized with a wireless capable hand-held device for data processing and storage. This point-of-care device can be capable of detecting a wide range of CSF concentrations by inserting the disposable test strip into the hand-held device, similar to blood glucose detection. The ability to function in highly ionic solutions is importance if whole blood, urine, nasal secretions, saliva, etc. are to be tested at the point-of-care. As has been discussed, short pulses of voltage to drain and gate electrodes can provide a detectable response of the antibody-protein complex. This pulse method allows the sensing area to be externalized away from the gate electrode of the HEMT; which permits reuse of the HEMT and simple swapping of a sensing strip.

Figure 8:
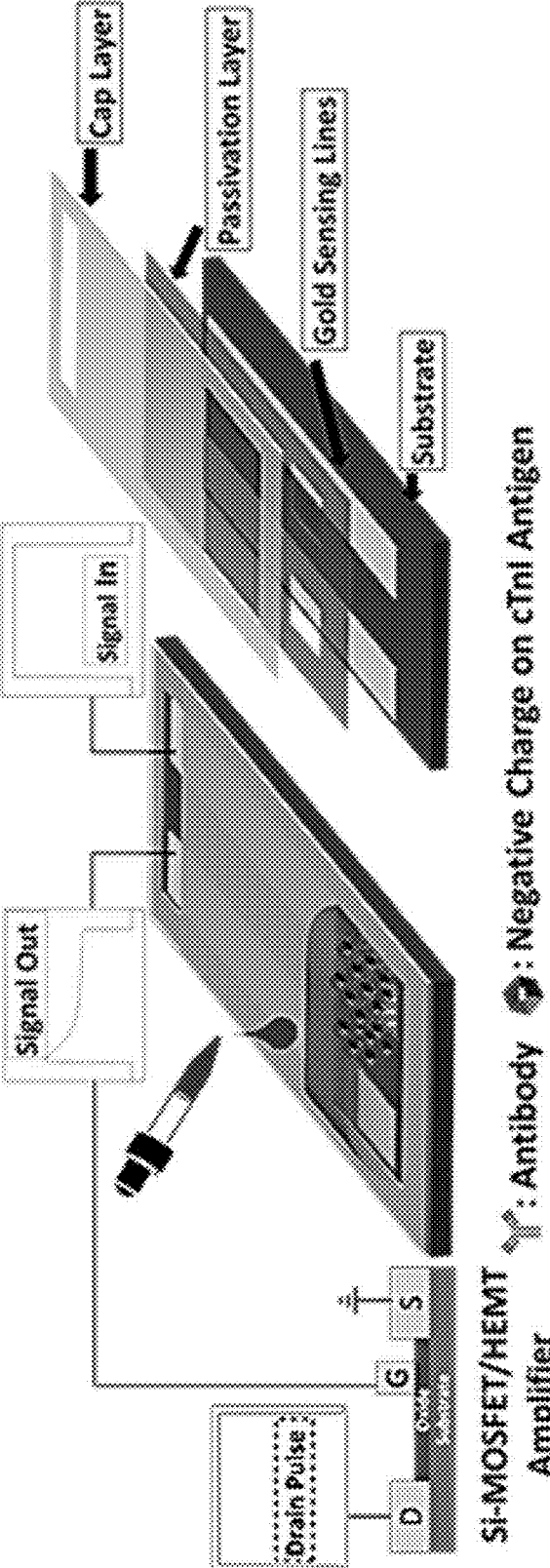
FIG. 8 illustrates an example of a disposable sensor, in accordance with various embodiments of the present disclosure.

An electrical double layer (EDL) gated FET biosensor capable of the direct detection of target analytes in physiological buffer solutions without extensive pretreatment or washing has been developed. FIG. 8 illustrates an example of the disposable sensor chip, including a substrate, sensing lines, passivation layer and cap layer. In this case, the electrode which has been functionalized with the target antibody is externally connected to the gate of the HEMT, as shown in FIG. 8. A window or opening allows a sample to be applied to the functionalized electrode. The substrate for sensor fabrication should have reasonable chemical and thermal resistance in order to withstand basic microfabrication processing. During photolithography and metal evaporation, temperatures of 75° C. or greater are common. In addition, the substrate should maintain its structure upon exposure to common solvents such as acetone and isopropyl alcohol.

A disposable plastic, glass, or paper cartridge strip can be used upon which the bodily fluid sample is placed. For example, polyethylene terephthalate (PET) satisfies the desired characteristics making it a suitable plastic for this application. Sensor chips can be fabricated from PET sheets with a thickness of 500 μm to 1 mm at a competitive cost. The PET sheet can be cut into pieces and sensor arrays can be fabricated on the PET sheets. A metallization of Cr/Ni/Au (10/100/100 nm) can be used for the electrical interconnects to provide adhesion and low resistance, respectively. AZ1818 photoresist (Microchem) can be used to pattern the interconnects, and electron-beam evaporation can be used to deposit Cr/Ni/Au. To use a clipper-based contact, a much thicker Au layer can be provided with an additional gold layer electroplated to ensure low resistance. Electroplating can deposit gold significantly faster and less expensively than alternative solutions. A seed layer of gold, 20 nm, can be evaporated over the entire sample and AZ4620 photoresist (Microchem) can be used to define the plating area. Approximately 5 μm of Au can be electroplated. After removing the photoresist with acetone, the seed layer can be etched off.

In other embodiments, ceramic substrates such as alumina may be used. Ceramic substrates have much better mechanical and electrical properties as compared to plastic and glass substrates. Among the ceramic substrate, alumina is very attractive due to lower cost as compared to other ceramics. The same process sequence and steps used on the glass slide can be employed to fabricate sensor chips on alumina. Since the dielectric constant of alumina is larger than that of glass, the effective capacitance of the sensor chip fabricated on the alumina would be larger than that of the glass.

To optimize sensor sensitivity and reduce cost, ensuring maximum binding of the antibody to the surface is important. For CSF sensing, a two-step functionalization can be used by treating the Au sensor surface with thioglycolic acid (TGA) and then binding the antibody to TGA through an amide formation between TGA and antibody. However, the direct conversion of a carboxylic acid to an amide can be difficult because amines are basic and tend to convert carboxylic acids to highly unreactive carboxylates. To improve binding efficiency, the carboxylic acid can be activated to form an amide via addition of a carbodiimide crosslinker, dicyclohexylbarbodimide (DDC). DCC induced coupling to form an amide linkage is a reaction in the synthesis of peptides. In this functionalization process, the carboxylic acid adds to the DCC molecule to form a good leaving group which can then be displaced by an amine during nucleophilic substitution. Improving the efficiency and stability of the bond between antibody and sensor is relevant to shelf life of the sensor strips and robustness of storage conditions they can endure without loss of activity, which will ultimately affect the calibration of the sensor and its output. Another method is to reduce the number of reactions from five in carbodiimide crosslinker down to two by using a different linker, which can be added directly with the antibody to the sensor.

For sensor functionalization with N-hydroxysuccinimide (NHS) and N,N'-Dicyclohexylcarbodiimide (DCC), the sensor can be treated with 1 mM thioglycolic acid for 24 hours. The sensor can first be submerged in 0.1 mM solution of DCC in dry acetonitrile for 30 minutes and then in 0.1 mM solution of NHS in dry acetonitrile for 1 hour. The sensor can then be treated with dilute antibody (1 μg/mL) in PBS for 12 hours. For sensor functionalization with thioglycolic acid (TGA) only, the sensor can be treated with 1 mM thioglycolic acid for 24 hours. The sensor can then be treated with dilute antibody (1 μg/mL) in PBS for 12 hours. For sensor functionalization with 4-(4,6-dimethoxy-1,3,5-triazin-2-yl)-4-methyl-morpholinium chloride (DMTMM), the sensor can be treated with 1 mM thioglycolic acid for 24 hours. The sensor can first be submerged in dilute antibody (1 μg/mL) and followed by dilute DMTMM (1 mM) in PBS for 12 hours.

With the externalized sensing chip approach, the HEMT can be repeatedly used, and the low-cost sensor chip is disposable. This cartridge can be inserted into a hand-held instrument containing associated electronics for readout, data recording and/or wireless transmission. The cartridge can be electrically connected to a printed circuit board (PCB) test specific module within the hand-held device.

Figure 9:
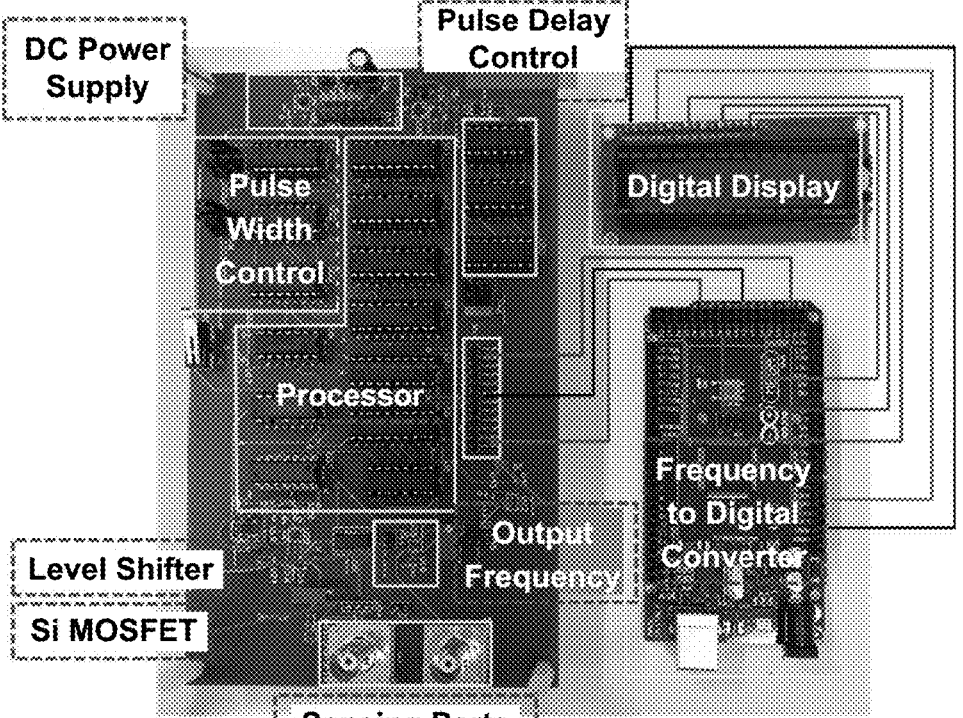
FIG. 9 is an image of a sensing device for sensing a condition using the disposable sensor of FIG. 8, in accordance with various embodiments of the present disclosure.

Another aspect of this approach is that there is no need to use an expensive AlGaN HEMT. The HEMT can be replaced with an inexpensive Si metal oxide field effect transistor (MOSFET), which can be integrated with integrated circuit technology to eliminate peripheral instruments for this measurement (e.g., pulse generators, etc.). PCBs including a Si MOSFET were designed and fabricated to remove the need for a parameter analyzer or oscilloscope. A digital readout was incorporated to make the final product simple to use and understandable for any user. FIG. 9 is an image of the prototype sensing device including a processor, digital display, frequency to digital converter, pulse controller and Si MOSFET. The PCBs are powered with a 9 V battery, and the dimensions of the PCBs are 4"×2", ½"×1.5", and 1"×2", respectively. The PCBs can be combined into one board of integrate circuits with advanced MOSFET technology. For hand-held applications, it is desirable to reduce these dimensions.

The circuit includes pulse generation, voltage level adjustment, and detection circuitry. Voltage level adjustment can allow for on-PCB variation of the applied gate voltage to the sensing chip in order to optimize sensing on a protein-by-protein basis, rather than designing a new PCB for every sensing target. Depending on a protein's length, net charge, and folding, the applied voltage can be tuned such that the protein-antibody complex is perturbed and undergoes a spring-like relaxation. If insufficient voltage is supplied there will be no perturbation of the protein-antibody complex. If excessive voltage is applied, there may be full elongation and dissociation of the protein-antibody complex. In either case sensing of the target protein will not occur repeatedly. The drain current can also be adjusted in order to alter the gate voltage of maximum transconductance. Additionally, in order to ensure detection at the lower limits of ng/mL, traces in the circuit were kept short in order to reduce noise from coupling.

The higher drain current corresponding to a 50 μs pulsed voltage applied to the electrode functionalized with cTnI antibody means that more positive charges are induced on the gate of transistor due to charge neutralization on the electrodes on the glass, solutions with different concentrations of cTnI and the negative charges carried on the antibody and cTnI. Since the isoelectric point of the cTnI is 5.8 to compare with the isoelectric point of 7.4 for the reference PBS, the cTnI would carry negative charges in the solutions with different cTnI concentrations applied on the contact windows of the glass. The opposite-polarity electrical double-layers are induced on both functionalized and unfunctionalized windows as a result of the positive 0.5 V of single pulse and native charges on the cTnI.

Due to charge neutralization in the solution with different cTnI concentrations, more positive charges with higher cTnI concentrations in the solution accumulate on the metal electrode contact window without the functionalized antibody, and negative charges are induced on the metal electrode next to the solution with more positive charges. Since this metal electrode is externally connected to the gate of the transistor, more positive charges are induced by the negative charges on the metal electrode next to the solution via charge neutralization on the metal. For a sample applied on the glass sample with higher cTnI concentrations, more cTnI molecules with negative charge will bind to the antibody molecules. Thus, the drain current increase is proportional to the cTnI concentration through charge neutralization, with more positive charge inducing more positive charges on the gate of transistor and producing higher drain currents.

Figure 10A:
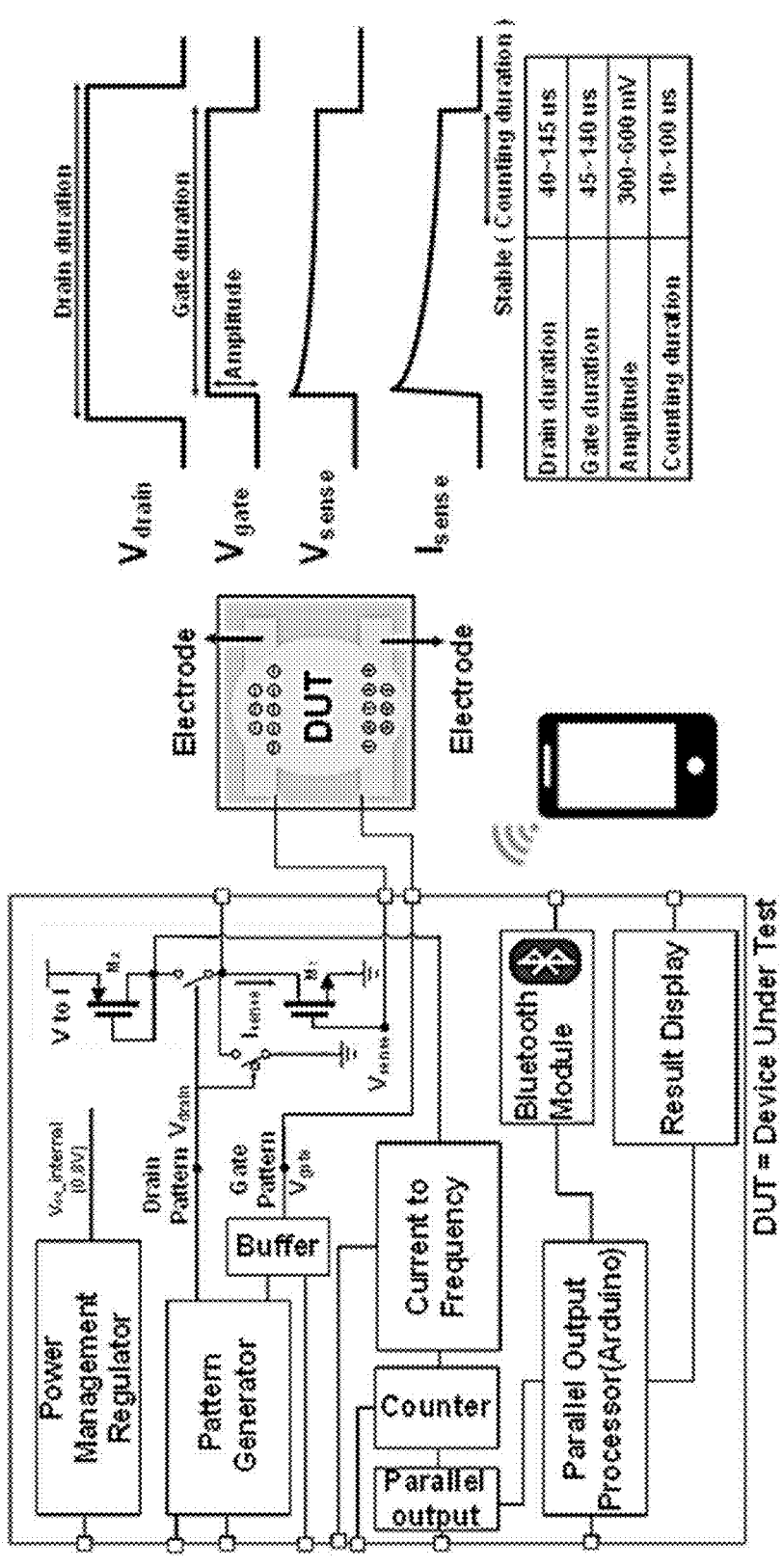
FIGS. 10A-10D include schematics and an image illustrating an example of circuitry for an integrated sensing device, in accordance with various embodiments of the present disclosure.

With advances of silicon technology, the biosensor readout circuitry can be integrated and fabricated into a single integrated chip (IC) to shrink the size for a hand-held device application and to avoid the wire coupling noise and signal losses. The size of the proposed integrated chip can be reduced to less than 1"×1", which is much compacted as compared to the size of a typical PCB board of around 3"×4". The proposed integrated chip may be fabricated in a commercially available foundry. FIG. 10A illustrates the architecture of the biosensor readout circuits, including power management units, reconfigurable pattern generator, current-to-frequency converter and digital signal processing units connected to the disposable sensor. The noise coupling and signal loss may limit the sensitivity of the sensor, especially for the extremely low bio-signal measurement. The approach of employing an IC can decrease the noise level. The sensing signal from the disposable sensor can be connected to the gate of the MOSFET via a clip-type connector as employed in a hand-held glucose monitor. A clip connector with six connectors can be used for multiple sensors.

Figure 10B:
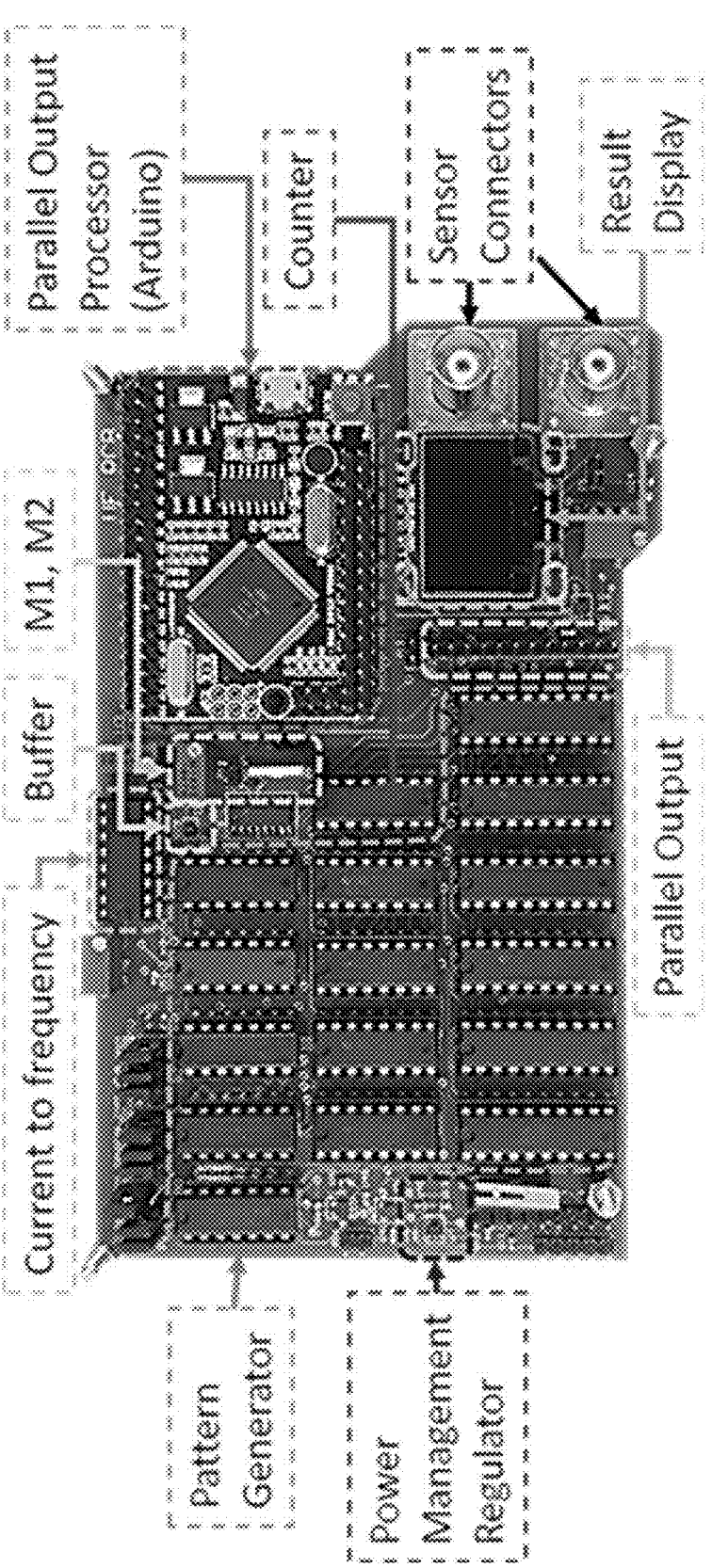

Besides using SPICE simulator to simulate the responses for the proposed integrated chip, prototype circuits with off-shelf components was adapted to verify the performance of the designed circuit and to optimize the design parameters. FIG. 10B is an image of the prototype design including readouts, microcontroller, signal processing units, and display. B&C connectors were used for the implemented design and can be replaced with strip clip connectors in the hand-held device. The detected signal can be converted to a frequency signal by an offset-cancellation RC oscillator, whose frequency only depends on the current and capacitor values. This approach will be less sensitive to the amplitude noise from the devices and voltage supply and can achieve low electrical noise and excellent stability. The frequency signal can be digitalized using a frequency counter. The frequency counter can provide intrinsic first-order noise shaping. By using digital architecture, high design flexibility, compact size, and low power consumption can be accomplished.

The pattern generator can stimulate the biosensor with a reconfigurable duration (40-145 µs), the delay time (5-100 µs) between the gate and drain stimuli, counting duration (10-100 µs) and amplitude (300-600 mV) to characterize the sensor performance, e.g., resolution, conversion time, and sensitivity. The bit-length of the frequency counter can control the bandwidth and sampling rate of the sensor readout circuit. Finally, for spectral efficiency and data security, the digital codes can be encoded into a packet series before wireless data communication. The design can integrate a Bluetooth® transceiver to communicate with a user device such as, e.g., a cellular phone or tablet. The user can record and analyze the test results immediately on the portable user device. The digitized readout signals can be sent to the onboard microcontroller and displayed on the LED screen directly, such as in a handheld bio-sensing reader.

Figures 10C, 10D:
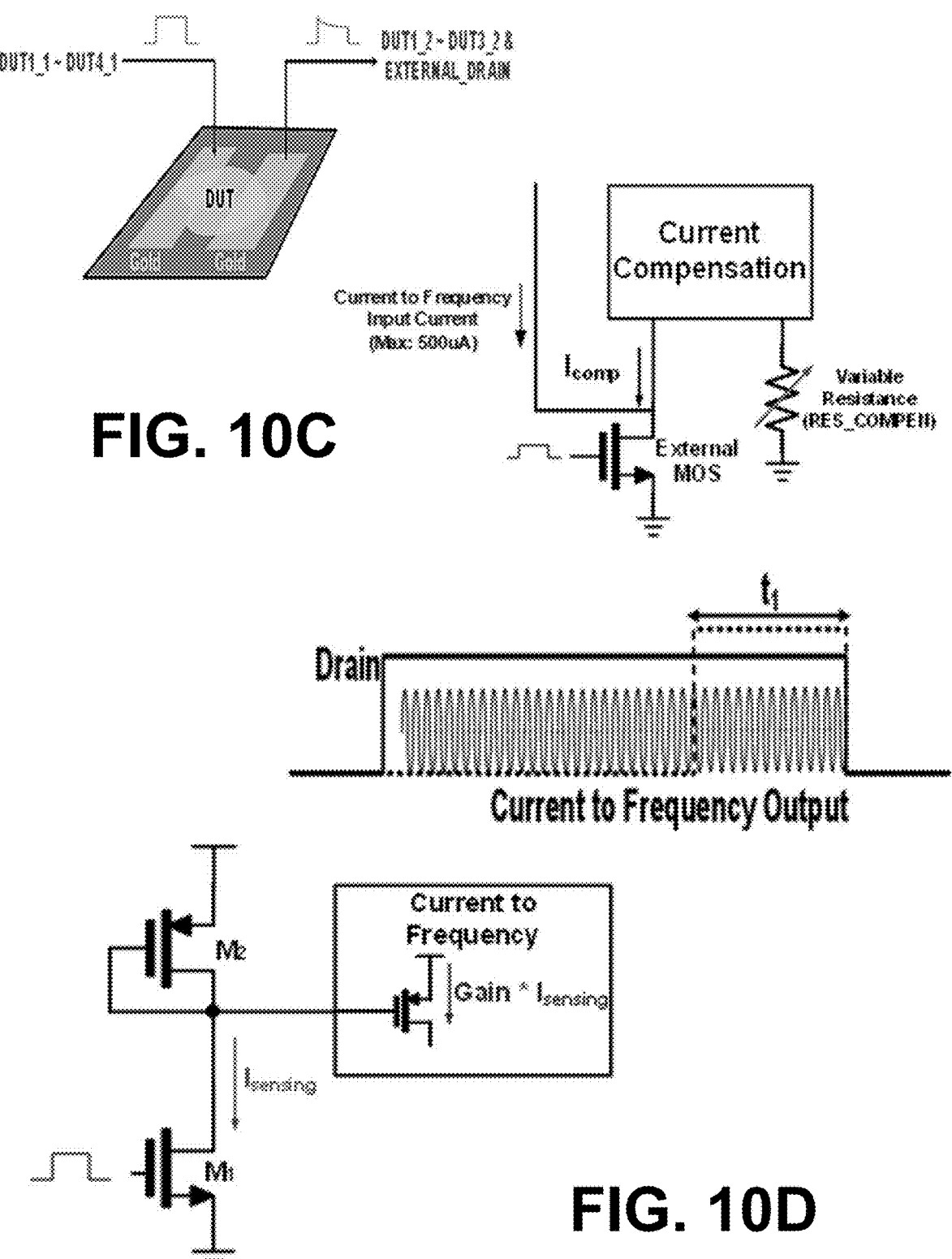

As shown in in FIG. 100, the pulsed signal is sent to the sensing chip, then to the gate electrode of the MOSFET on the PCB board. FIG. 100 includes a schematic diagram illustrating the current to frequency block with a variable resistor that can be used to determine a current to improve the sensing response. Once the value of the resistor determined, this information can be used to design the IC chip. In order to employ wireless transmission, the detected analog signals can be converted into digital signals, as illustrated in FIG. 10D. An example of a circuit that can be used for transforming analog to digital signals is shown.

Figure 11:
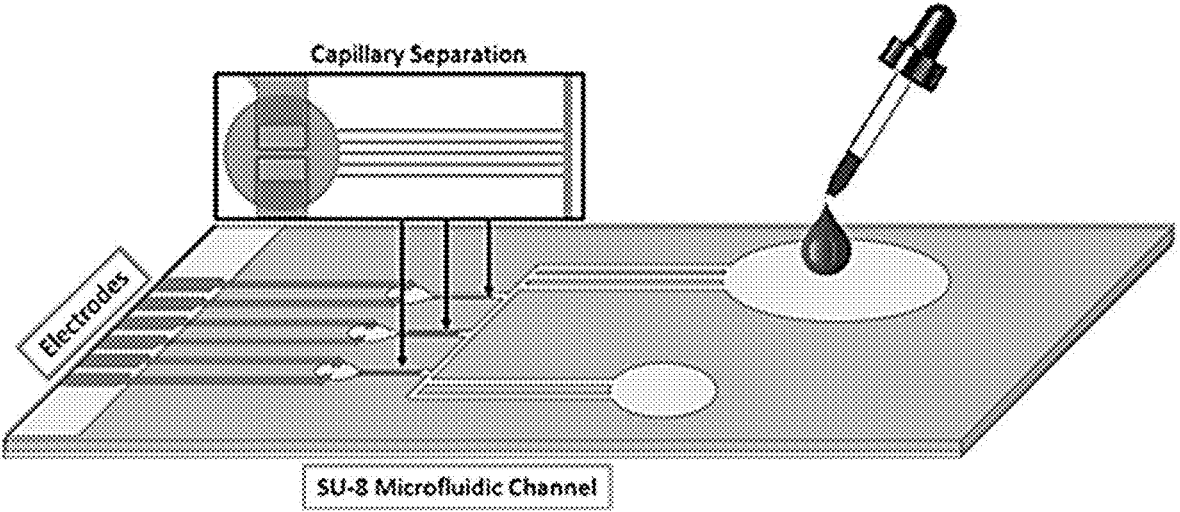
FIG. 11 is a schematic illustrating an example of a disposable sensor comprising multiple microfluidic channels configured with a plurality of sensing electrodes, in accordance with various embodiments of the present disclosure.

Microfluidics based blood component separation can be employed to avoid membrane clogging and compromise separation efficiency, especially for the application of small sample volumes. FIG. 11 is a schematic illustrating an example of a disposable sensor comprising multiple microfluidic channels fabricated on, e.g., a plastic substrate configured with a plurality of sensing electrodes. A sample can be provided in a sample deposit window or opening of the sensor and allowed to propagate down the microfluidic channels to one or more functionalized sensing areas, where it can be analyzed, and the result shown on a hand-held instrument as previously disclosed. In some implementations, separate windows can be provided for each of the functionalized sensing areas. The sensing methodology is based on the externalized sensing chip approach previously described.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1% to about 5%, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:
1. A medical sensing system, comprising:
a disposable sensing unit comprising:
    a substrate;
    first and second electrodes disposed on the substrate; and
    a functionalized sensing area disposed between the first and second electrodes on the substrate without a transistor between the first and second electrodes, the functionalized sensing area functionalized with an anti β-2-transferrin antibody; and
a portable sensing unit analyzer comprising:
    pulse generation circuitry configured to generate synchronized gate and drain pulses, the first electrode of the disposable sensing unit electrically coupled to a gate pulse output of the pulse generation circuitry; and
    a transistor having a drain electrically coupled to a drain pulse output of the pulse generation circuitry, and a gate electrically coupled to the second electrode of the disposable sensing unit.
2. The medical sensing system of claim 1, wherein the anti β-2-transferrin antibody is bound to the functionalized sensing area by a binding agent disposed on the first electrode.

3. The medical sensing system of claim 2, wherein the binding agent is thioglycolic acid (TGA, HSCH$_2$COOH).

4. The medical sensing system of claim 1, wherein the first and second electrodes comprise a passivation layer of photoresist.

5. The medical sensing system of claim 4, wherein the passivation layer comprises an opening exposing the functionalized sensing area.

6. The medical sensing system of claim 1, wherein the transistor is a Si metal oxide semiconductor field effect transistor (MOSFET).

7. The medical sensing system of claim 1, wherein the transistor is a GaAs MESFET, an InP FET, a heterojunction bipolar transistor, a SiCMOS transistor, a SiGe FET, a biCMOS transistor or an III-V semiconductor based high electron mobility transistor (HEMT).

8. The medical sensing system of claim 7, wherein the III-V semiconductor based HEMT is a GaAs, InAlAs or InGaAs based HEMT.

9. The medical sensing system of claim 1, wherein the functionalized sensing area is disposed between the first and second electrodes and comprises at least one end of the first electrode and at least one end of the second electrode.

10. The medical sensing system of claim 9, wherein the functionalized sensing area is disposed between the first and second electrodes and comprises one end of the first electrode and one end of the second electrode.

11. The medical sensing system of claim 1, wherein the first and second electrodes are Ni/Au based metal electrodes disposed on the substrate.

12. The medical sensing system of claim 1, wherein the substrate comprises a ceramic strip, a paper strip or a plastic strip.

13. The medical sensing system of claim 12, wherein the plastic strip is a polyethylene terephthalate (PET) strip.

14. The medical sensing system of claim 1, wherein the disposable sensing unit comprises microfluid channels extending between a sample deposit opening and the functionalized sensing area.

15. The medical sensing system of claim 14, wherein disposable sensing unit comprises a plurality of functionalized sensing areas.

\* \* \* \* \*